United States Patent
Cha et al.

(10) Patent No.: US 9,316,655 B2
(45) Date of Patent: Apr. 19, 2016

(54) BIOCHEMICAL ANALYSIS CARTRIDGE HAVING IMPROVED OPERABILITY

(71) Applicant: I-SENS, INC., Seoul (KR)

(72) Inventors: Geun Sig Cha, Seoul (KR); Hakhyun Nam, Seoul (KR); Dongxuan Shen, Incheon (KR); Joo Young Cho, Incheon (KR); Jihoon Kim, Gyeonggi-do (KR)

(73) Assignee: I-SENS, INC., Seoul (KR)

( * ) Notice: Subject to any disclaimer, the term of this patent is extended or adjusted under 35 U.S.C. 154(b) by 0 days.

(21) Appl. No.: 14/608,564

(22) Filed: Jan. 29, 2015

(65) Prior Publication Data

US 2015/0147804 A1     May 28, 2015

Related U.S. Application Data

(63) Continuation of application No. PCT/KR2013/003752, filed on Apr. 30, 2013.

(30) Foreign Application Priority Data

Jul. 31, 2012 (KR) ........................ 10-2012-0084183

(51) Int. Cl.
*C12M 1/34* (2006.01)
*C12M 3/00* (2006.01)
(Continued)

(52) U.S. Cl.
CPC .............. *G01N 33/726* (2013.01); *B01L 3/502* (2013.01); *G01N 33/54366* (2013.01);
(Continued)

(58) Field of Classification Search
CPC ................... B01L 2300/045; B01L 2300/047; B01L 2300/0672; B01L 2300/0816; B01L 2300/0835; B01L 2300/0867; B01L 2400/0457; B01L 2400/0683; B01L 3/502; G01N 33/54366; G01N 33/723; G01N 33/726
See application file for complete search history.

(56) References Cited

U.S. PATENT DOCUMENTS

| 5,162,237 | A  | 11/1992 | Messenger et al. |
| 2009/0093012 | A1 | 4/2009 | Bae et al. |

FOREIGN PATENT DOCUMENTS

| CN | 1534296 | 10/2004 |
| CN | 101408549 | 4/2009 |

(Continued)

OTHER PUBLICATIONS

International Search Report prepared by the Japanese Patent Office on Aug. 6, 2013, for International Application No. PCT/KR2013/003752.

*Primary Examiner* — Michael Hobbs
(74) *Attorney, Agent, or Firm* — Sheridan Ross, P.C.

(57) ABSTRACT

The present invention relates to a biochemical analysis cartridge having improved operability. More particularly, the present invention provides a biochemical analysis cartridge including an insertion-type sample cartridge and a reaction cartridge receiving the insertion-type sample cartridge, in which, as the sample cartridge is inserted into the reaction cartridge, a reaction solution chamber moves toward a broken part of a covertape so as to automatically supply the reaction solution stored in the chamber. The biochemical analysis cartridge having improved operability according to the present invention can induce the mixing between a sample and a reaction solution by simply inserting them into the reaction cartridge and a reaction thereafter, thereby minimizing the process of a measurer to intervene in the assay, and subsequently improving user convenience and operability.

9 Claims, 5 Drawing Sheets

(51) Int. Cl.
G01N 33/72 (2006.01)
G01N 33/543 (2006.01)
B01L 3/00 (2006.01)

(52) U.S. Cl.
CPC ........ *G01N 33/723* (2013.01); *B01L 2300/045* (2013.01); *B01L 2300/047* (2013.01); *B01L 2300/0672* (2013.01); *B01L 2300/0816* (2013.01); *B01L 2300/0835* (2013.01); *B01L 2300/0867* (2013.01); *B01L 2400/0409* (2013.01); *B01L 2400/0457* (2013.01); *B01L 2400/0683* (2013.01)

(56) References Cited

FOREIGN PATENT DOCUMENTS

| | | |
|---|---|---|
| CN | 201654027 | 11/2010 |
| EP | 2047909 | 4/2009 |
| EP | 2353718 | 8/2011 |
| JP | 07-055661 A | 3/1995 |
| JP | 2005-204614 A | 8/2005 |
| JP | 2009-219824 A | 10/2009 |
| KR | 10-0662021 B1 | 12/2006 |
| KR | 10-0776394 B1 | 11/2007 |
| WO | WO 93/16391 | 8/1993 |

<BEFORE INSERTING SAMPLE CARTRIDGE>  <AFTER INSERTING SAMPLE CARTRIDGE>

BIOCHEMICAL ANALYSIS CARTRIDGE HAVING IMPROVED OPERABILITY

CROSS-REFERENCE TO RELATED APPLICATIONS

This application is a continuation application under 35 U.S.C. §120 of International Application No. PCT/KR2013/003752 filed Apr. 30, 2013, which claimed the benefit of Korean Patent Application No. 10-2012-0084183 filed Jul. 31, 2012, the entire contents of each of which are incorporated herein by reference.

TECHNICAL FIELD

The present disclosure relates to a biochemical analysis cartridge having improved operability capable of optically measuring with ease the amount and the concentration of a particular sample through a liquid reaction between one or more assay reagents and a small amount of a bio-sample, and particularly, to a biochemical analysis cartridge having improved operability that requires almost no input by a user.

BACKGROUND ART

Currently, in the medical diagnosis field, in order to detect or quantify a particular sample contained in a bio-sample such as blood, serum, urine, and cell sap, various assay technologies such as enzyme assay, immunoassay, chemical colorimetric assay, electrochemical assay, fluorescence labeling and measurement, and chemiluminescent labeling and measurement are used. The assay technologies are applied and used in large apparatuses such as automatic assay devices used in clinical trial centers of hospitals, or point-of-care testing (POCT) devices using platforms such as test strips and cartridges.

The large automatic apparatuses have advantages in that a large quantity of samples can be treated at high speed and the reliability of measured values is high. However, there are disadvantages in that the mechanical structures of the apparatuses are complicated and the apparatuses can be used only in special examination rooms, which limit the number of locations in which they can be installed. Further, the apparatuses often require pretreatment of the bio-samples and periodic replacement of various types of reagents and sensors, thus making it very cumbersome to maintain and manage the apparatuses.

Meanwhile, in the case of the point-of-care testing device, the reliability of the measured values is rather low compared to those of the large apparatuses. However, the ability to take measurements is not limited in terms of location, and the measurement can be rapidly performed, which enables the POCT devices to be extensively used in the medical diagnosis field. Particularly, unlike the large apparatuses in which various types of reagents and sensors should be respectively equipped and installed, the cartridge-type point-of-care testing device constitutes a bio-sample supply unit, a reaction reagent, and a detection unit in one cartridge, thus providing high user convenience during measurement. Further, due to a low risk of contamination through exposure to the bio-sample after measurement, the device is favorable in terms of stability.

Meanwhile, for diagnosing diabetes, there is a growing demand for the point-of-care testing of glycated hemoglobin along with blood-sugar measurement. Glycated hemoglobin (HbAlc) refers to a hemoglobin bound to glucose. The measurement of glycated hemoglobin contained in blood not only provides an average blood-sugar value of a patient for the past three to four months regardless of meals and the physical state of the patient but also helps to evaluate the efficiency of the blood-sugar management method employed by the patient, thus drawing much public attention to the necessity of measuring glycated hemoglobin. In fact, numerous reports on cartridge-type point-of-care testing devices for measuring glycated hemoglobin contained in blood have been released.

U.S. Pat. No. 6,300,142 B1 discloses a cartridge for measuring an analyte by reacting a sample with a first reactant through a first inlet and subsequently reacting the sample with a second reactant through a second inlet in order to measure the glycated hemoglobin level in blood. However, in this case, measurements should sequentially occur at time intervals and a measurer should intervene in the measurement step to ensure that the samples can be sequentially injected to react. Further, there are problems in that a reagent solution may be leaked during the measurement process, thus deteriorating the reliability and marketability of the measurement result, and also that it requires pre-filtration of the beads combined with glycated hemoglobin, thus making the measurement complicated and require a longer time. Additionally, since the process requires direct intervention of a user in various steps, the user may feel encumbered, which naturally delays the measurement time.

Further, U.S. Pat. No. 7,632,462 B2 discloses an analysis cartridge including at least two well spaces and a pipette which may be positioned in at least the two well spaces. In this case, the pipette has a stylobate unit and an end unit, and the end unit has a structure which is closed by a membrane through which a liquid can permeate. Further, the patent discloses an assay device including a holder disposed to receive the cartridge, a driving unit operated to position the pipette in the selected well space in the cartridge, a gas pressure application device combined with the pipette to fluidize the liquid in the pipette through the membrane, a radiation detector detecting radiation from the well spaces or the pipette of the cartridge to be operated, and an electromagnetic radiation source. The assay device is a cartridge-type point-of-care testing device for glycated hemoglobin having a high quantitative property, but has disadvantages in that structures of the cartridge and the assay device are too complicated as described above to embody a driving system, thus increasing the cost of the assay device.

Accordingly, the present inventors developed a biochemical analysis cartridge including an insertion sample cartridge for supplying a bio-sample and a reaction cartridge including one or more reaction units capable of fixing one or more assay reagent and reacting the assay reagents with the solution reagent, and a measurement window capable of performing optical measurement, thereby completing the present invention.

DISCLOSURE OF THE INVENTION

Technical Problem

One object of the present invention is to provide a biochemical analysis cartridge having improved operability.

Technical Solution

In order to achieve the object, the present invention provides a biochemical analysis cartridge including an insertion sample cartridge for supplying a sample and a reaction cartridge receiving the insertion sample cartridge, wherein the reaction cartridge may include: a receiving unit into which the insertion sample cartridge is inserted to be received; a chamber for storing a reaction solution, provided inside the receiving unit with an opening at one end, including a cover tape attached to the opening to prevent the discharge of the stored reaction solution, and provided so that the opening to which the cover tape is attached faces the inside of the reaction cartridge; a cover tape breaking unit provided to oppose the cover tape of the chamber for storing the reaction solution so as to be distant from the cover tape; a chamber moving frame which fixes the chamber for storing the reaction solution and includes a moving path through which the chamber for storing the reaction solution moves toward the cover tape breaking unit; and a mixing unit receiving the discharged reaction solution when the cover tape is removed and mixing the reaction solution and a a discharged bio-sample by contacting the reaction solution with a sample inlet of the insertion sample cartridge to form a mixed solution; a reagent fixing unit to which a reagent is fixed to react with the mixed solution of the mixing unit; a measurement unit optically measuring a result of the reaction; and a flow path through which the mixing unit, the reagent fixing unit, and the measurement unit are connected; and the insertion sample cartridge includes: a capillary sample injection unit for collecting and storing a liquid phase bio-sample which has a sample inlet for supplying the stored bio-sample to the reaction cartridge; and a protrusion which contacts the chamber for storing a reaction solution of the reaction cartridge to move the chamber for storing a reaction solution to the cover tape breaking unit when the insertion sample cartridge is inserted into the receiving unit.

Advantageous Effect

A biochemical analysis cartridge according to the present invention has an advantage in that the chamber for storing the reaction solution is provided inside of the reaction cartridge such that the reaction solution stored in the chamber is automatically supplied simultaneously when the insertion sample cartridge is inserted through the reaction cartridge. Thus, it is possible to improve convenience by minimizing the intervention of a user in the assay. Additionally, it has an advantage in that, by applying gravity and a cartridge rotation system, the bio-sample supplied from the insertion sample cartridge and the reaction solution supplied from the chamber can be respectively fluidized along the flow path into each reaction unit thereby simplifying the operation process, and through the same, user convenience and the operability of the analysis cartridge are improved.

DESCRIPTION OF REFERENCE NUMERALS

Figure 1:
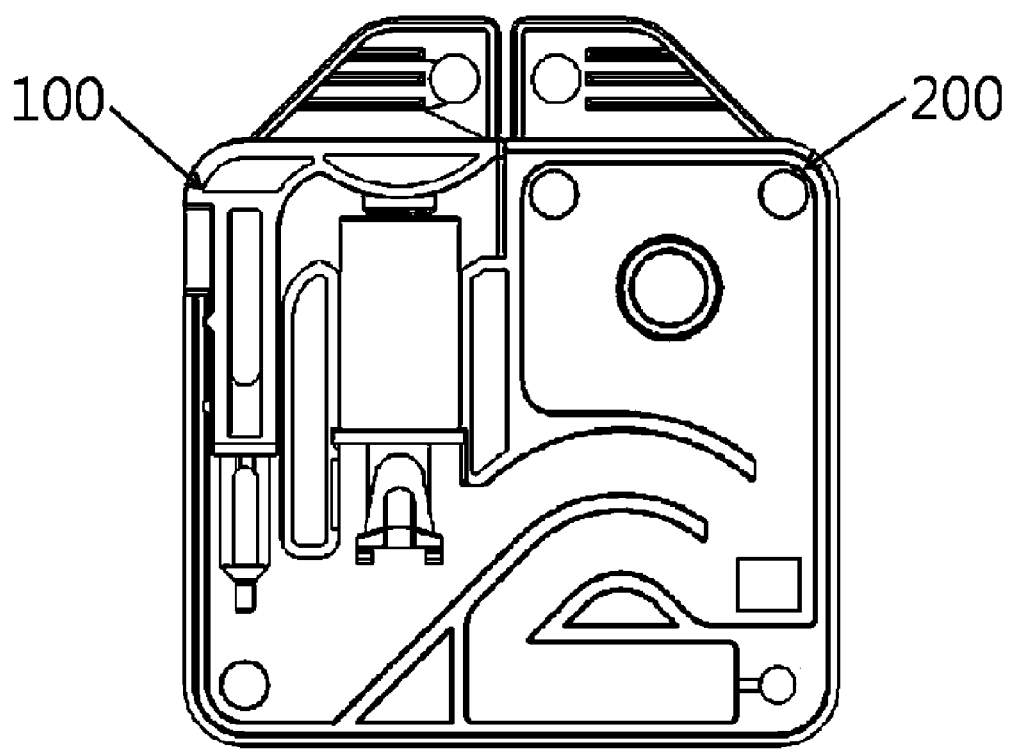
FIG. 1 is a front perspective view showing a biochemical analysis cartridge according to the present invention.

100: injection-type sample cartridge
101: sample injection unit
102: protrusion
103: sample cartridge handle
104: clamp
200: reaction cartridge
201: receiving unit
202: cover tape breaking unit
203: chamber moving frame
204: mixing unit
205: reagent fixing unit
206: flow path
207: measurement unit
208: waste liquid treatment unit
209: air outlet
210: reaction cartridge handle
211: fixing groove
301: chamber for storing reaction solution
302: cover tape

MODE FOR CARRYING OUT THE INVENTION

Hereinafter, the most preferred embodiment of the present invention will be described with reference to the accompanying drawings in order to describe the present invention in detail so that the technical spirit of the present invention can be easily embodied by those skilled in the art to which the present invention belongs. First, it is to be noted that in assigning reference numerals to elements in the drawings, the same reference numerals designate the same elements throughout the drawings although the elements are shown in different drawings. In addition, in the description of the present disclosure, the detailed descriptions of known related constitutions or functions thereof may not be included if their inclusion is thought to make the gist of the present invention unclear.

The present invention provides a biochemical analysis cartridge including an insertion sample cartridge for supplying a sample and a reaction cartridge receiving the insertion sample cartridge, wherein the reaction cartridge includes: a receiving unit into which the insertion sample cartridge is inserted to be received; a chamber for storing a reaction solution, provided inside the receiving unit with an opening at one end, including a cover tape attached to the opening to prevent the discharge of the stored reaction solution, and provided such that the opening to which the cover tape is attached faces the inside of the reaction cartridge; a cover tape breaking unit provided to oppose the cover tape of the chamber for storing the reaction solution and provided to be distant from the cover tape; a chamber moving frame which fixes the chamber for storing the reaction solution and includes a moving path through which the chamber for storing the reaction solution moves toward the cover tape breaking unit; and a mixing unit receiving the discharged reaction solution when a protective film is removed and mixing the reaction solution and a discharged bio-sample by contacting the reaction solution with a sample inlet of the insertion sample cartridge to form a mixed solution; a reagent fixing unit where a reagent is fixed to react with the mixed solution of the mixing unit; a measurement unit optically measuring a result of the reaction; and a flow path through which the mixing unit, the reagent fixing unit, and the measurement unit are connected; and the insertion sample cartridge includes: a capillary sample injection unit for collecting and storing a liquid phase bio-sample which has a sample inlet for supplying the stored bio-sample to the reaction cartridge; and a protrusion which contacts the chamber for storing a reaction solution of the reaction cartridge to move the chamber for storing a reaction solution to the cover tape breaking unit when the insertion sample cartridge is inserted into the receiving unit.

The biochemical analysis cartridge according to the present invention will be described in detail through the drawings.

Referring to FIGS. 1 to 4, the biochemical analysis cartridge according to the present invention includes an insertion sample cartridge 100 for supplying the sample and a reaction cartridge 200 into which the insertion sample cartridge is inserted to be received. In particular, the reaction cartridge 200 includes a receiving unit 201, into which the insertion sample cartridge 100 is inserted, and a mixing unit 204, in which the bio-sample, discharged from the sample cartridge inserted through the receiving unit, is mixed with the reaction solution.

Additionally, the reaction cartridge 200 includes one or more of a reagent fixing unit 205 into which a chemical reagent, which can induce an enzyme reaction and an antigen/antibody reaction by reacting with a mixed reaction solution and a bio-sample mixed in the mixing unit 204, is introduced, and the assay of the bio-sample can be performed via optical analysis such as UV/VIS in a measurement unit 207, in which the result of the reaction performed in the reagent fixing unit 205 is measured.

Additionally, the reaction cartridge 200 includes a chamber 301 for storing a reaction solution, in which the reaction solution capable of reacting with the bio-sample is stored. The chamber 301 for storing a reaction solution is provided with an opening at one end, and a cover tape 302 is attached to the opening to prevent the discharge of the stored reaction solution. Additionally, the chamber 301 for storing a reaction solution is provided so that the opening to which the cover tape 302 is attached can face toward the inside of the reaction cartridge 200. That is, the chamber 301 for storing a reaction solution is provided so that the discharged reaction solution can be moved into the mixing unit 204 inside the reaction cartridge 200 when the stored reaction solution is discharged due to the removal or breakage of the cover tape 302.

Meanwhile, the chamber 301 for storing a reaction solution, which is provided inside the reaction cartridge 200, may be fixed to a chamber moving frame 203, and the chamber moving frame 203 includes a moving path through which the chamber 301 for storing a reaction solution can move.

Additionally, the reaction cartridge 200 includes a cover tape breaking unit 202 so that the cover tape 302, attached to the opening of the chamber for storing a reaction solution, can be removed or broken, and the cover tape breaking unit 202 is provided to oppose the cover tape 302 in the chamber for storing a reaction and to be distant from the cover tape.

That is, as the chamber 301 for storing a reaction solution moves toward the cover tape breaking unit 202 through the chamber moving frame 203, the cover tape 302 in the chamber 301 for storing a reaction comes in contact with the cover tape breaking unit 202 to be removed or broken. As the cover tape is removed or broken, the reaction solution that is discharged from the chamber 301 for storing a reaction is moved to the mixing unit 204 to be mixed with the bio-sample supplied from the sample cartridge 100.

In particular, the form of the chamber 301 for storing a reaction is not particularly limited as long as it has a structure for easy storage of the reaction solution, and the material of the cover tape 302 is also not particularly limited as long as it is a material which can be easily removed or broken.

Additionally, the cover tape breaking unit 202 is not particularly limited as long as it has a structure to easily remove or break the cover tape, and preferably, it may be in the form of a needle or edge, but is not limited thereto.

Additionally, the reaction cartridge 200 includes a flow path 206 through which the reaction solution and the bio-sample mixed in the mixing unit 204 can move. Through the flow path 206, the mixing unit 204, one or more of the reagent fixing unit 205, and the measuring unit 207 for measuring the reaction result between the bio-sample and the reaction solution can move. The structure of the flow path 206 is not particularly limited as long as it has a structure designed so that the reaction solution and the bio-sample can move by gravity when the reaction cartridge 200 is tilted.

Additionally, the reaction cartridge 200 may further include a waste liquid treatment unit 208 for collecting a waste liquid measured in the measurement unit 207. The waste liquid as a kind of medical waste may be collected and separately treated through the waste liquid treatment unit 208, and the collection of the waste liquid through the waste liquid treatment unit may be performed by adding cotton wool, an absorptive filter, and an absorptive raw material made of a polymer having strong absorptivity to the waste liquid treatment unit 208 to absorb the waste liquid.

The reaction cartridge 200 may further include an air outlet 209. The air outlet 209 is a structure to facilitate the movement of the waste liquid and absorption of the absorption raw material, and the waste liquid may be more smoothly moved to the waste liquid treatment unit 208 therethrough and the absorption for collecting the waste liquid may be more smoothly performed therethrough.

Meanwhile, in the biochemical analysis cartridge according to the present invention, the insertion sample cartridge 100 includes a capillary sample injection unit 101 for collecting a bio-sample for assay in a needed amount and for storage. The bio-sample is collected through a capillary tube provided in the sample injection unit 101 and is simultaneously injected into the reaction cartridge 200. In particular, the amount of the bio-sample can be regulated by adjusting the inner volume according to the inner diameter and height of the capillary tube at the sample injection unit, and the structure of the sample injection unit is not limited to a capillary tube as long as it has a structure for easy discharge of the bio-sample.

Additionally, the insertion sample cartridge 100 includes a protrusion 102 that contacts the chamber 301 for storing a reaction solution provided inside the reaction cartridge and pushes the chamber 301 for storing a reaction solution into the reaction cartridge when the insertion sample cartridge 100 is inserted in the receiving unit 201 of the reaction cartridge 200. The protrusion 102 is provided in the insertion sample cartridge 100 to a position to be able to contact the chamber 301 for storing a reaction solution when the insertion sample cartridge 100 is inserted into the reaction cartridge 200, and moves the chamber 301 for storing a reaction solution toward the inside of the reaction cartridge 200 so that the cover tape 302 of the chamber 301 for storing a reaction solution is removed or broken by the cover tape breaking unit 202 simultaneously as the insertion sample cartridge 100 is inserted.

Figure 5:
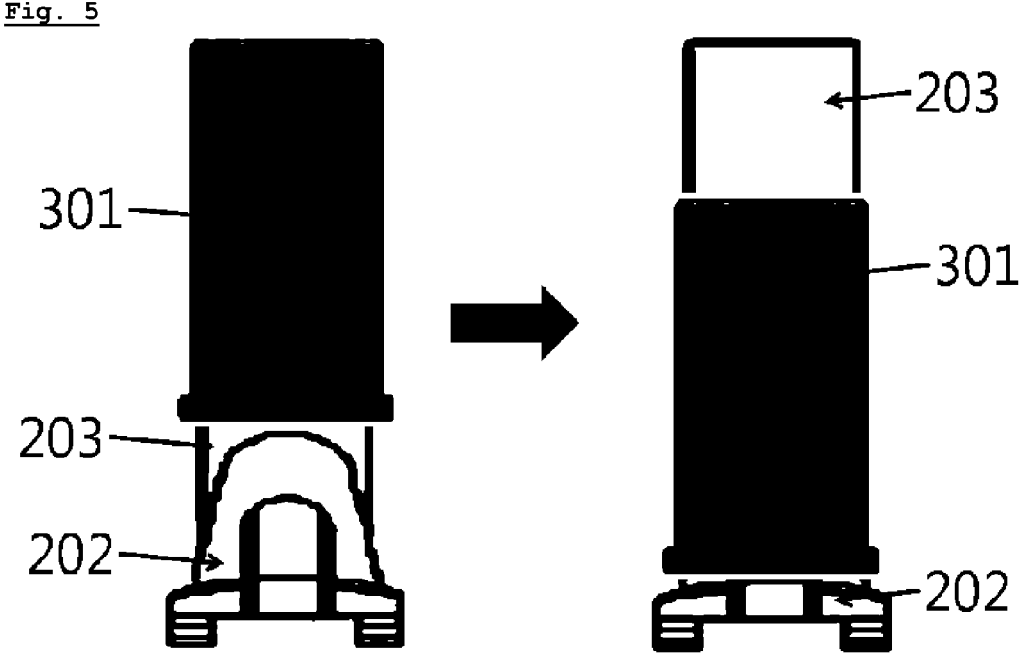
FIG. 5 is a schematic view showing a sample cartridge, before and after its insertion, of the biochemical analysis cartridge according to the present invention.

That is, as shown in FIG. 5, the chamber 301 for storing a reaction solution is moved by the protrusion 102 toward the cover tape breaking unit 202 simultaneously as the insertion sample cartridge 100 is inserted into the reaction cartridge 200, and accordingly, the reaction solution is discharged from the chamber 301 for storing a reaction solution and is moved to the mixing unit 204.

The reaction solution automatically discharged from the chamber 301 for storing a reaction solution by inserting the sample cartridge 100 into the reaction cartridge 200 comes in contact with the sample injection unit 101, and through the contact, the bio-sample is also discharged into the mixing unit 204 of the reaction cartridge 200 through the sample injection unit 101 and mixed with the reaction solution. Accordingly, in the biochemical analysis cartridge according to the present invention, although a measurer does not intervene in the injection process of the sample and the injection process of the reaction solution, the bio-sample and the reaction solution are automatically injected and mixed, thus improving user convenience and operability. Additionally, since the chamber 301 for storing a reaction solution is provided inside the reaction cartridge 200, the discharge of the reaction solution into the outside before insertion of the insertion of the sample cartridge may be prevented.

Meanwhile, the sample cartridge 100 and the reaction cartridge 200 may further include a sample cartridge handle 103 and a reaction cartridge handle 210, respectively. The handles are configured to easily move and use the sample cartridge 100 and the reaction cartridge 200, and the structures thereof are not particularly limited.

Additionally, when the sample cartridge 100 is inserted into the reaction cartridge 200, in order to fix the sample cartridge 100, a clamp 104 may be provided on a side of the sample cartridge and a fixing groove 211 may be provided on the receiving unit of the reaction cartridge. The clamp 104 may engage with the fixing groove 211 to fix the inserted sample cartridge 100 to the reaction cartridge 200. Although the biochemical analysis cartridge of the present invention rotates, movement or separation of the sample cartridge due to performing assay may be prevented.

Figure 2:
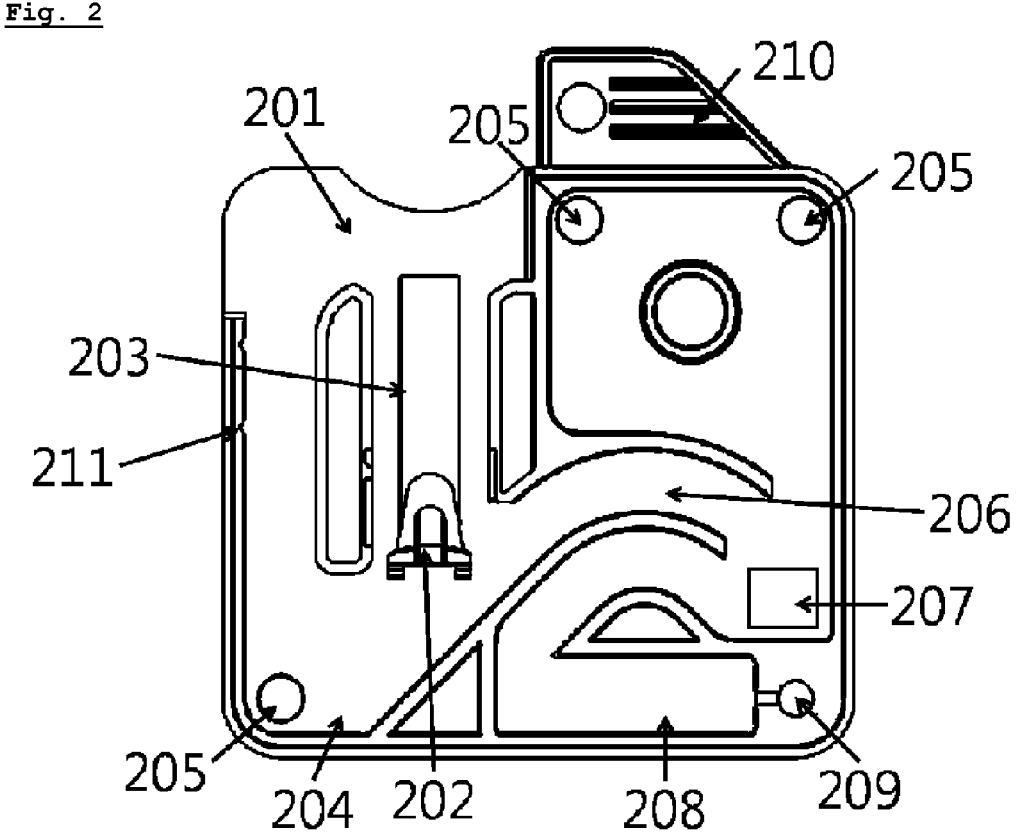
FIG. 2 is a front perspective view showing a reaction cartridge of the biochemical analysis cartridge according to the present invention.
Figure 3:
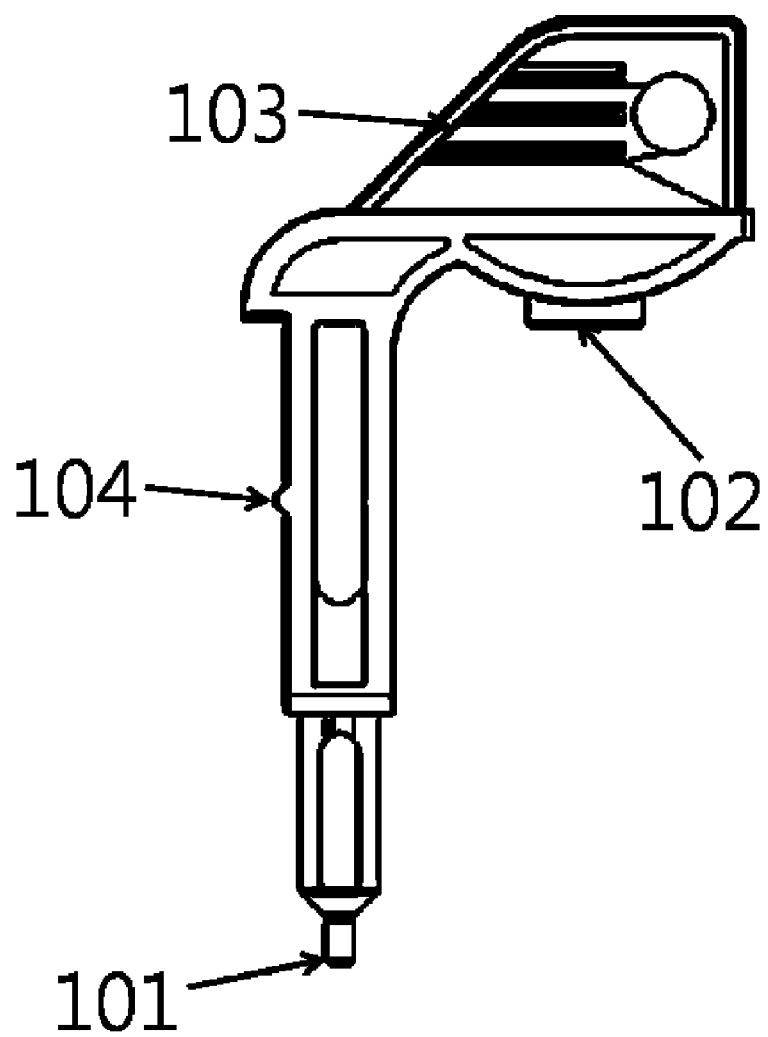
FIG. 3 is a diagram showing a chamber for storing a reaction solution provided inside the reaction cartridge according to the present invention.
Figure 4:
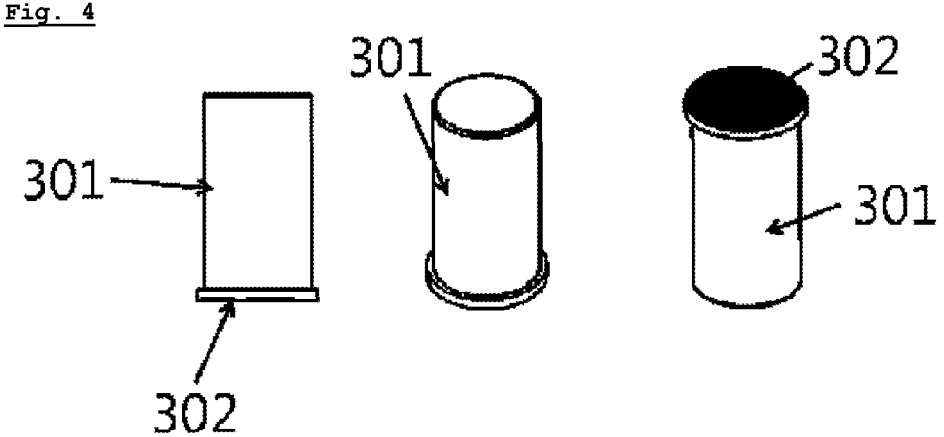
FIG. 4 is a diagram an insertion sample cartridge of the biochemical analysis cartridge according to the present invention.

The biochemical analysis cartridge according to the present invention moves the bio-sample and the reaction solution along the flow path influenced by gravity due to rotation into the measurement unit and the sample introduction unit, and accordingly, the reaction between the reaction solution and the bio-sample and the measurement are performed. In particular, the structure of the flow path, the position of the reagent fixing unit, and the number of the reagent fixing unit illustrated in FIGS. 1 and 2 are shown as an example for performing the assay for the bio-sample, and the biochemical analysis cartridge according to the present invention is not limited thereto.

The biochemical analysis cartridge according to the present invention may be used for the assay of various bio-samples, preferably for the assay of blood, and more preferably for the quantitative assay of glycated hemoglobin.

For example, the quantitative assay of glycated hemoglobin through an enzymatic method using the biochemical analysis cartridge according to the present invention will be described in detail.

The enzymatic method for the quantitative assay of glycated hemoglobin mainly consists of four chemical reactions.

The first reaction is a hemolytic reaction of a blood sample, which refers to a reaction where erythrocytes in blood are destroyed via dissociation of hemoglobin using the reaction solution. In particular, the reaction solution used for the purpose of hemolytic reaction may be manufactured through various methods such as pH adjustment and the use of a surfactant.

The second reaction is a reaction to cleave glycated hemoglobin molecules using a proteolytic enzyme, and various enzymes such as protease A, protease N, dispase, pronase, neutral protease, Glu-C, papain, trypsin, and pepsin may be used.

The third reaction is a reaction where generated glycated peptide or glycated amino acid molecules digested by proteolytic enzyme are oxidated using an oxidase called fructosyl peptide oxidase (FPOX), and hydrogen peroxide may be generated therefrom.

The fourth reaction is a color reaction, which refers to a chemical reaction where hydrogen peroxide ($H_2O_2$) generated by the third reaction is oxidated using peroxidase (POD), and a color developing reagent and the substrate are reduced by electrons emitted from oxidation, thus being discolored.

In order to perform the quantitative assay for glycated hemoglobin by the enzymatic method, the four reactions are performed in the biochemical analysis cartridge according to the present invention, and the quantitative assay for glycated hemoglobin will be described in detail as an example through the structures and an operating method of the cartridge illustrated in FIGS. 1 to 5.

In order to perform an assay, blood is collected and stored in the sample injection unit 101 of the insertion sample cartridge 100. Then, the insertion sample cartridge 100 is inserted into the receiving unit 201 of the reaction cartridge 200, the chamber 301 for storing a reaction solution is moved through the chamber moving frame 203 by the protrusion 102, and the cover tape 302 attached to the chamber 301 for storing a reaction solution is brought into contact with the cover tape breaking unit 202, such that the reaction solution in the storage chamber is discharged and moved to the mixing unit 204. The discharged solution is brought into contact with the sample injection unit 101 of the insertion sample cartridge 100 and mixed with a blood sample to perform the hemolytic reaction between the blood sample and the reaction solution. Upon completion of the hemolytic reaction, in a first reagent fixing unit to which one type of a reagent among the proteolytic enzyme, FPOX, and POD is fixed, the fixed reagent is dissolved by the blood sample, and the enzyme reaction may be induced therefrom.

The hemolytic reaction is performed in the mixing unit 204, and the reaction solution, in which the enzyme reaction has been completed by the first sample fixing unit, is moved to the measurement unit 207 along the flow path 206 in the reaction cartridge due to gravity and rotation of the cartridge. The reaction solution moved to the measurement unit 207 is used to measure the total hemolytic hemoglobin using absorbance exhibited at 535 nm via a UV-Vis spectrophotometer.

The reaction solution, in which the measurement of total hemoglobin has been completed, is moved to a second reagent fixing unit through the rotation of the cartridge. The second reagent fixing unit was constituted to have a face-to-face structure, to which a reagent including the remaining two enzymes that are mixed (other than the enzyme fixed to the first reagent fixing unit) and a color developing reagent are fixed, and in which the reagent of the two enzymes and the color developing reagent face each other.

The reaction solution moved to the second reagent fixing unit is subjected to both the enzyme reaction and the color reaction, and the reaction solution, in which both the enzyme reaction and the color developing reaction have been completed, is moved back to the measurement unit 207 through the rotation of the cartridge. Subsequently, the concentration of glycated hemoglobin colored by the color reaction is measured using absorbance exhibited around 660 nm via a UV-Vis spectrophotometer.

Upon completion of the assay, the waste liquid is moved to the waste liquid treatment unit 208 through the rotation of the cartridge, and the waste liquid is absorbed through the absorption raw material in the waste liquid treatment unit 208 to be collected.

As described above, spectrophotometry should be performed twice for the quantitative assay of glycated hemoglobin because glycated hemoglobin refers to the ratio of glycated hemoglobin to the concentration of total hemoglobin. That is, the assay process is cumbersome in that it includes many steps such as the pretreatment of a blood sample by a measurer and the attaching of a marker material. However, when the assay of glycated hemoglobin is performed using the biochemical analysis cartridge according to the present invention, the enzyme reaction can be performed and absolute concentrations of total hemoglobin and glycated hemoglobin can be measured in one cartridge by moving the reaction solution through the rotation of the cartridge. In particular, the reaction solution (a hemolytic reagent in the case of a glycated hemoglobin assay) may be automatically discharged to the mixing unit in the reaction cartridge while the insertion sample cartridge 100 is inserted into the mixing unit of the reaction cartridge, such that direct intervention by a person performing an assay in an assay process can be minimized and problems such as delays in an assay time or a decrease in assay precision can be prevented. Additionally, since the chamber 301 for storing a reaction solution is provided inside of the reaction cartridge 200, the discharge of the reaction solution to the outside before the insertion of the sample cartridge 100 may be prevented.

While descriptions have been provided above of preferred embodiments according to the present invention, modifications in various forms are possible. It will be understood by those with ordinary skill in the art of the present technical field that various modified examples and amended examples may be practiced without departing from the scope of the claims of the present invention.

The invention claimed is:

1. A biochemical analysis cartridge comprising an insertion sample cartridge for supplying a sample and a reaction cartridge receiving the insertion sample cartridge, wherein
the reaction cartridge includes:
a receiving unit into which the insertion sample cartridge is inserted to be received;
a chamber for storing a reaction solution, provided inside the receiving unit with an opening at one end, including a cover tape attached to the opening to prevent the discharge of the stored reaction solution, and provided such that the opening to which the cover tape is attached faces the inside of the reaction cartridge;
a cover tape breaking unit provided to oppose the cover tape of the chamber for storing the reaction solution and provided to be distant from the cover tape;
a chamber moving frame fixing the chamber for storing the reaction solution and including a moving path through which the chamber for storing the reaction solution moves toward the cover tape breaking unit; and
a mixing unit receiving the discharged reaction solution when the cover tape is removed and mixing the reaction solution and a discharged bio-sample by contacting the reaction solution with a sample inlet of the insertion sample cartridge to form a mixed solution;
a reagent fixing unit where a reagent is fixed to react with the mixed solution of the mixing unit;
a measurement unit optically measuring a result of the reaction; and
a flow path through which the mixing unit, the reagent fixing unit, and the measurement unit are connected; and
the insertion sample cartridge includes:
a capillary sample injection unit for collecting and storing a liquid phase bio-sample which has a sample inlet for supplying the stored bio-sample to the reaction cartridge; and
a protrusion which contacts the chamber for storing a reaction solution of the reaction cartridge to move the chamber for storing a reaction solution to the cover tape breaking unit when the insertion sample cartridge is inserted into the receiving unit.

2. The biochemical analysis cartridge as set forth in claim 1, wherein the chamber for storing a reaction solution moves toward the cover tape breaking unit to break the cover tape at the same time when the insertion sample cartridge is inserted into the reaction cartridge.

3. The biochemical analysis cartridge as set forth in claim 1, wherein the reaction cartridge includes a plurality of reagent fixing units.

4. The biochemical analysis cartridge as set forth in claim 1, wherein the reaction is an enzyme reaction between a substrate in the mixed solution and an enzyme in the sample, or an antigen-antibody reaction between an antigen in the mixed solution and an antibody in the sample.

5. The biochemical analysis cartridge as set forth in claim 1, wherein the mixed solution of the bio-sample and a chemical reagent is moved along the flow path to the measurement unit or the reagent fixing unit by gravity and centrifugal force caused by rotation of the entire biochemical analysis cartridge.

6. The biochemical analysis cartridge as set forth in claim 1, wherein the reaction cartridge of the biochemical analysis cartridge further includes a waste liquid treatment unit for treating the mixed solution of the bio-sample, the reaction solution, and the chemical reagent after measurement.

7. The biochemical analysis cartridge as set forth in claim 6, wherein the reaction cartridge of the biochemical analysis cartridge further includes an air outlet for smooth movement and collection of the waste liquid.

8. The biochemical analysis cartridge as set forth in claim 1, wherein the biochemical analysis cartridge is a biochemical analysis cartridge for blood assay.

9. The biochemical analysis cartridge as set forth in claim 1, wherein the biochemical analysis cartridge is a biochemical analysis cartridge for glycated hemoglobin quantitative assay.

* * * * *